US006372790B1

(12) United States Patent
Bonhomme et al.

(10) Patent No.: US 6,372,790 B1
(45) Date of Patent: Apr. 16, 2002

(54) PHARMACEUTICAL COMPOSITION COMPRISING A COMBINATION OF METFORMIN AND FIBRATE, AND ITS USE FOR THE PREPARATION OF MEDICINES INTENDED TO REDUCE HYPERGLYCAEMIA

(75) Inventors: Yves Bonhomme, Charbonnieres les Bains; Philippe Briet, Lyons, both of (FR)

(73) Assignee: Merck Patent Gesellschaft mit beschrankter Haftung, Darnstadt (DE)

( * ) Notice: Subject to any disclaimer, the term of this patent is extended or adjusted under 35 U.S.C. 154(b) by 0 days.

(21) Appl. No.: 09/601,618
(22) PCT Filed: Jan. 30, 1999
(86) PCT No.: PCT/EP99/00614
  § 371 Date: Nov. 30, 2000
  § 102(e) Date: Nov. 30, 2000
(87) PCT Pub. No.: WO99/40904
  PCT Pub. Date: Aug. 19, 1999

(30) Foreign Application Priority Data

Feb. 12, 1998 (FR) .............................................. 98/01709

(51) Int. Cl.[7] ...................... A61K 31/205; A61K 31/195
(52) U.S. Cl. ......................... 514/555; 514/563; 514/866
(58) Field of Search ................................ 514/563, 866, 514/555

(56) References Cited

U.S. PATENT DOCUMENTS

| 4,080,472 A | 3/1978 | Bohuon ....................... 524/316 |
| 5,304,575 A | 4/1994 | Beck ........................... 514/563 |

FOREIGN PATENT DOCUMENTS

| EP | 0 305 890 | 3/1989 |
| FR | 2 264 525 | 10/1975 |
| WO | 98/05331 | * 2/1998 |

OTHER PUBLICATIONS

S.R. De Silva et al.: "Metformin and clofibrate in maturity onset diabletes mellitus: advantages of combined treatment." Diabetes Metabol., vol. 5, No. 3, 1979, pp. 223–229.

Liu et al., "An animal model for testing hypoglycemic and hypolipidemic drugs", Yaoxue Xuebao (1994), 29(5), pp. 387–389 (abstract enclosed).*

* cited by examiner

*Primary Examiner*—Kevin E. Weddington
(74) *Attorney, Agent, or Firm*—Millen, White, Zelano & Branigan, P.C.

(57) ABSTRACT

A pharmaceutical composition comprising: (i) metformin, optionally in the form one of its pharmaceutically acceptable salts; (ii) a fibrate selected from fenofibrate and bezafibrate; and optionally one or more pharmaceutically acceptable excipients, is suitable for use in the treatment of non-insulin-dependent diabetes.

21 Claims, No Drawings

PHARMACEUTICAL COMPOSITION COMPRISING A COMBINATION OF METFORMIN AND FIBRATE, AND ITS USE FOR THE PREPARATION OF MEDICINES INTENDED TO REDUCE HYPERGLYCAEMIA

The invention relates to a pharmaceutical composition containing a combination of metformin and of a fibrate chosen from fenofibrate and bezafibrate, as active principles. The invention also relates to the use of metformin and of a fibrate chosen from fenofibrate and bezafibrate for the preparation of a medicinal combination intended to reduce the hyperglycaemia of non-insulin-dependent diabetes.

Metformin is mainly known for its anti-hyperglycaemic activity and is widely used in the treatment of non-insulin-dependent diabetes. In the case of insulin-dependent diabetes, metformin is also administered to the patient in combination with insulin.

Bezafibrate and fenofibrate belong to the family of fibrates whose anti-hyperlipidic properties are well known. More specifically, the fibrates act on hypercholesterolaemia and hypertriglyceridaemia by inducing a reduction in the total cholesterol level as well as the cholesterol linked to low density lipoproteins (LDL-cholesterol) and an even greater reduction in the levels of triglycerides and in particular of triglycerides linked to very low density lipoproteins (VLDL-triglycerides).

Bezafibrate has already been administered to non-insulin-dependent diabetics on account of its hypolipaemic properties. This is because non-insulin-dependent diabetes is often accompanied by serious lipid metabolism disorders; consequently, one of the main causes of mortality of patients suffering from this type of diabetes is the appearance of coronary diseases or disorders of the cerebrovascular system or of the peripheral vascular system which can lead to myocardial infarction.

The value of a treatment with bezafibrate in the case of diabetics suffering from non-insulin-dependent diabetes has been reported in particular by P. W. Seviour et al. in Diabetic Medicine, Vol. 5, 166–171 (1988).

The combination of a hypoglycaemic agent and of an anti-lipaemic agent has already been envisaged in the art, and especially for treating diabetics also displaying hyperlipaemia. Contradictory results were obtained depending on the nature of the active substances. The study by A. K. Jain et al. published in Diabetes, Vol. 34, 1985, Vol. 293 (25), 1283 shows, for example, that better control of the hyperglycaemia is obtained by joint administration of sulphonylurea (hypoglycaemic agent) and of halogenate (antilepaemic agent). However, that document reveals the absence of an effect of clofibrate (a known antilipaemic agent) on the seric glucose level in diabetic patients treated simultaneously with sulphonylurea.

Among the studies relating to combined therapies, mention may also be made of the combination of metformin and clofibrate proposed by S. R. De Silva et al. in Diabete & Metabolisme, 1979, 5, 223–229. That author notes a slight improvement in the hypoglycaemia on simultaneous administration of clofibrate and metformin. However, the essential advantage of this combination lies manifestly in the parallel reduction of the levels of cholesterol and of triglycerides. It thus results from that publication that the overall effect of the combination is the simple addition of the respective effects of each of the active substances.

Surprisingly, the present inventors have discovered that a specific combination of a hypoglycaemic agent with an antilipaemic agent leads to a significant improvement of the hyperglycaemia in a diabetic patient suffering from non-insulin-dependent diabetes. More specifically, a synergistic effect has been obtained by combined administration of metformin and of a fibrate chosen from fenofibrate and bezafibrate. The same advantageous results have been observed using a pharmaceutically acceptable salt of metformin in combination with one of these two fibrates.

The synergistic effect observed lies in a marked improvement of the hypoglycaemia, this being found both in patients with hyperlipaemia and in non-dyslipidaemic patients.

Thus, the invention relates to a pharmaceutical composition comprising, as active principles, (i) metformin optionally in the form of one of its pharmaceutically acceptable salts, and (ii) a fibrate chosen from fenofibrate and bezafibrate, in combination with one or more pharmaceutically acceptable excipients.

This composition is more particularly suitable for reducing the hyperglycaemia of non-insulin-dependent diabetes. It can also be used on non-dyslipidaemic patients.

According to the invention, the metformin can be administered in the form of one of its pharmaceutically acceptable salts, such as the hydrochloride, acetate, benzoate, citrate, fumarate, embonate, chlorophenoxyacetate, glycolate, palmoate, aspartate, methanesulphonate, maleate, parachlorophenoxyisobutyrate, formate, lactate, succinate, sulphate, tartrate, cyclohexanecarboxylate, hexanoate, octonoate, decanoate, hexadecanoate, octodecanoate, benzenesulphonate, trimethoxybenzoate, paratoluenesulphonate, adamantanecarboxylate, glycoxylate, glutamate, pyrrolidonecarboxylate, naphthalenesulphonate, 1-glucosephosphate, nitrate, sulphite, dithionate or phosphate.

Among these salts, the hydrochloride, fumarate, embonate and chlorophenoxyacetate are more particularly preferred.

The pharmaceutically acceptable salts of metformin are obtained in a manner which is known per se by the action of metformin on the corresponding acid.

The compositions of the invention contain therapeutically effective amounts of the various active principles. The ratios of the respective amounts of metformin and of fibrate thus vary in consequence.

Preferably, the weight ratio of metformin or of its pharmaceutically acceptable salt to fibrate ranges from 1:1 to 20:1, preferably from 1:1 to 5:1 and better still from 2:1 to 5:1.

The compositions of the invention are preferably administered parenterally, or better still orally, although the other routes of administration, for instance such as rectal administration, are not excluded.

When oral administration is envisaged, the compositions of the invention are in the form of gelatin capsules, effervescence tablets, coated or uncoated tablets, sachets, sugar-coated tablets, drinkable vials or solutions, microgranules or sustained-release forms.

When parenteral administration is envisaged, the compositions of the invention are in the form of injectable solutions and suspensions packaged in vials or bottles for slow venous infusion.

The forms for oral administration are prepared by mixing the active substance with various types of excipients or of vehicles, such as fillers, disintegration (or crumbling) agents, binders, dyes, flavour enhancers and the like, followed by shaping the mixture.

The dye can be any dye authorized for pharmaceutical use.

Examples of flavour enhancers include cocoa powder, mint, borneol and cinnamon powder.

Examples of binders which may be mentioned are polyvinylpyrrolidone, hydroxypropylmethylcellulose, alginic acid, carbomer, carboxymethylcellulose, dextrin, ethylcellulose, starch, sodium alginate, polymethacrylate, maltodextrin, liquid glucose, magnesium aluminium silicate, hydroxyethylcellulose, ethylcellulose, methylcellulose and guar gum.

It is possible to use alginic acid, sodium carboxymethylcellulose, colloidal silicon dioxide, sodium croscarmellose, crospovidone, guar gum, magnesium aluminium silicate, methylcellulose, microcrystalline cellulose, potassium polacrilin, cellulose powder, pregelatinized starch, sodium alginate or sodium starch glycolate as disintegration agent.

The fillers are, for example, cellulose, lactose, calcium hydrogenophosphate and microcrystalline cellulose.

The tablets can be obtained in a conventional manner by compressing granules in the presence of one or more lubricants. Suitable lubricants are calcium stearate, glyceryl monostearate, glyceryl palmitostearate, hydrogenated castor oil, hydrogenated plant oil, light mineral oil, magnesium stearate, polyethylene glycol, sodium benzoate, sodium lauryl sulphate, stearyl sodium fumarate, stearic acid, talc and zinc stearate. These tablets can then be coated using polymers in solution or suspension, such as hydroxypropylmethylcellulose or ethylcellulose.

The granules used to do this are prepared, for example, by using the wet-route granulation process starting with a mixture of the active principles with one or more excipients such as a binder, a crumbling agent (or disintegration agent) and a filler.

To obtain hard capsules, the mixture of active principles with a suitable filler (for example lactose) is incorporated into empty gelatin capsules optionally in the presence of a lubricant such as magnesium stearate, stearic acid, talc or zinc stearate.

Soft gelatin capsules are prepared by dissolving the active principles in a suitable solvent (for example polyethylene glycol), followed by incorporation into soft capsules.

The forms for parenteral administration are obtained in a conventional manner by mixing the active principles with buffers, stabilizers, preserving agents, solubilizing agents, tonicity agents and suspension agents. In accordance with the known techniques, these mixtures are subsequently sterilized and then packaged in the form of intravenous injections.

As buffer, a person skilled in the art can use buffers based on salts of organic phosphate.

Examples of suspension agents include methylcellulose, hydroxyethylcellulose, acacia and sodium carboxymethylcellulose.

Examples of solubilizing agents include castor oil solidified with polyoxyethylene, polysorbate 80, nicotinamide or macrogol.

In addition, stabilizers which are useful according to the invention are sodium sulphite and sodium metasulphite, while mention may be made of sodium p-hydroxybenzoate, sorbic acid, cresol and chlorocresol as preserving agents. For the preparation of an oral solution or suspension, the active principles are dissolved or suspended in a suitable vehicle with a dispersing agent, a wetting agent, a suspension agent (for example polyvinylpyrrolidone), a preserving agent (such as methylparaben or propylparaben), a flavour enhancer or a dye.

For the preparation of suppositories, the active principles are mixed in a manner which is known per se with a suitable base constituent, such as polyethylene glycol or semi-synthetic glycerides.

For the preparation of microcapsules, the active principles are combined with suitable diluents, suitable stabilizers, agents which promote sustained release of the active substances or any other type of additive for the formation of a central core which is then coated with a suitable polymer (for example a water-soluble resin or a water-insoluble resin). The techniques known to those skilled in the art will be used for this purpose.

The microcapsules thus obtained are then optionally formulated in suitable dosage units.

A subject of the present invention is also the use of metformin optionally in the form of one of its pharmaceutically acceptable salts in combination with a fibrate chosen from bezafibrate and fenofibrate, for the preparation of a medicinal combination intended to reduce the hyperglycaemia of non-insulin-dependent diabetes.

According to another of its aspects, the invention relates to the use of metformin optionally in the form of one of its pharmaceutically acceptable salts, in combination with the said fibrate, for the preparation of a medicinal combination intended to reduce the hyperglycaemia of non-insulin-dependent diabetes in non-dyslipidaemic patients.

According to the invention, the term "medicinal combination" is intended to refer either to a pharmaceutical composition as defined above, in which the two active principles are the essential constituents of the same composition, or to a kit comprising two separate compositions, the first comprising metformin or its pharmaceutically acceptable salt as sole active principle, and the second comprising fibrate as sole active principle.

When the medicinal combination is in the form a kit, the administration of the two compositions constituting this kit, although carried out separately, is simultaneous for a combined treatment.

The metformin can be in the form of any one of the salts defined above; however, it is preferred to use metformin as it is or in the form of the hydrochloride, fumarate, embonate or chlorophenoxyacetate.

According to a preferred embodiment, the amount of metformin or of its salt which is used is from one to twenty times the mass of the fibrate, preferably from one to five times and better still from two to five times.

When the metformin or its salt and the fibrate are incorporated into the same unit dose, the unit dose preferably comprises from 100 to 1000 mg of metformin.

In this case, the unit dose advantageously comprises from 50 to 300 mg of fenofibrate or from 50 to 600 mg of bezafibrate.

The dosage naturally depends on the mode of administration, the therapeutic indication and the patient's age and condition.

In general, the daily dosage ranges between 100 and 2000 mg of metformin, between 50 and 600 mg of fenofibrate and between 50 and 1200 mg of bezafibrate.

The use of the compositions of the invention and the advantage of the use claimed are illustrated hereinbelow with reference to the example which follows.

EXAMPLE

The synergism of action was proven using an animal model. Non-insulin-dependent diabetes (NIDD) is induced by injecting streptozotocin into male wistar rats. The action of clofibrate alone, of bezafibrate alone, of fenofibrate alone and of metformin alone was first evaluated in terms of glycaemia, cholesterol level and level of triglycerides. Next, the metformin+clofibrate, metformin+bezafibrate and metformin+fenofibrate combinations were studied.

The procedure followed is as follows.

45 mg/kg of streptozotocin (STZ) dissolved in physiological saline are administered to male Wistar rats. Two weeks after this treatment, blood is taken and the glycaemia is measured. Only the animals with a glycaemia of between 2 grams and 3 grams per litre are used for the treatments (about 6/10). The animals then receive, orally, either metformin alone, or a fibrate alone, or a combination of the two in the doses indicated in Table 1 below. 23 days after the injection of streptozotocin, the animals are sacrificed and the following parameters are determined: glycaemia, cholesterol and triglycerides. The averages obtained from 10 rats per group are modified by the standard error of the mean. The Student t test is carried out to evaluate the significance of the results obtained.

The combined results are reported in Table 1 below:

TABLE 1

| Treatment | Glycaemia g/l | Cholesterol g/l | Triglycerides g/l |
|---|---|---|---|
| Absolute control | 1.06 ± 0.06 | 0.50 ± 0.02 | 0.86 ± 0.04 |
| Streptozotocin alone | 2.68 ± 0.06$^{\circ\circ}$ | 0.65 ± 0.04$^{\circ\circ}$ | 1.25 ± 0.07$^{\circ\circ}$ |
| Metformin (50 mg/kg) | 1.74 ± 0.14** | 0.61 ± 0.03 | 0.85 ± 0.10** |
| Clofibrate (100 mg/kg) | 2.58 ± 0.11 | 0.63 ± 0.03 | 0.93 ± 0.11* |
| Fenofibrate (50 mg/kg) | 1.92 ± 0.20** | 0.45 ± 0.02** | 0.61 ± 0.10** |
| Bezafibrate (50 mg/kg) | 2.20 ± 0.21* | 0.52 ± 0.05** | 0.81 ± 0.11** |
| Clofibrate (100 mg/kg) + Metformin (50 mg/kg) | 1.72 ± 0.09** | 0.63 ± 0.02 | 0.94 ± 0.08** |
| Fenofibrate (50 mg/kg) + Metformin (50 mg/kg) | 1.44 ± 0.11** | 0.56 ± 0.05 | 0.63 ± 0.12** |
| Bezafibrate (50 mg/kg) + Metformin (50 mg/kg) | 1.43 ± 0.05**§ | 0.48 ± 0.04**§ | 0.62 ± 0.02**§ |

$^{\circ}p > 0.01$ Comparison between absolute controls and NIDD STZ rats
*$p > 0.05$,
**$p > 0.01$ Comparison between control and treated STZ
§$p > 0.05$ Comparison between metformin alone and in combination Examination of the results obtained quite clearly shows the synergism of action of the (metformin+fenofibrate) or (metformin+bezafibrate) combination on glycaemia. Whereas metformin alone leads to a glycaemia of 1.74 g/l and bezafibrate alone leads to a glycaemia of 2.20 g/l and fenofibrate alone leads to a glycaemia of 1.92 g/l, the metformin+bezafibrate/fenofibrate combinations lead, respectively, to glycaemias of 1.43 g/l and 1.44 g/l.

On the other hand, no synergism is observed for the clofibrate+metformin combination; in fact, the resulting glycaemia of 1.72 g/l is virtually that resulting from the administration of clofibrate.

Interestingly, it is more noted that:

the fibrates, in particular bezafibrate and fenofibrate, when administered alone, show evidence of antihyperglycaemic properties. This effect may be associated with the enzymatic inductive effects by the action on glucose-6-phosphatase (action correlated with the variation of antipyrine);

metformin, administered alone, possesses, besides its antidiabetic activity, effects on decreasing the levels of cholesterol and of triglycerides (in animals, such as in man).

This example unequivocally illustrates the surprising effect observed during the simultaneous administration of metformin and of a fibrate chosen from fenofibrate and bezafibrate.

What is claimed is:

1. A pharmaceutical composition comprising: (i) metformin optionally in the form of one of its pharmaceutically acceptable salts; (ii) a fibrate chosen from fenofibrate and bezafibrate; and one or more pharmaceutically acceptable excipients.

2. A pharmaceutical composition according to claim 1, wherein the weight ratio of metformin or of its pharmaceutically acceptable salt to fibrate is 1:1 to 20:1.

3. A pharmaceutical composition according to claim 1, wherein metformin is in the form of a salt which is a hydrochloride, fumarate, embonate or chlorophenoxyacetate.

4. A pharmaceutical composition according to claim 1, where the weight ratio of metformin or of its pharmaceutically acceptable salt to fibrate is 2:1 to 5:1.

5. A pharmaceutical composition according to claim 1, wherein the weight ratio of metformin or its pharmaceutically acceptable salt to fibrate is 1:1 to 5:1.

6. A composition according to claim 2, wherein said composition contains 100–1000 mg of metformin and 50–300 mg of fenofibrate.

7. A composition according to claim 1, wherein said composition contains 100–1000 mg of metformin and 50–600 mg of bezafibrate.

8. A composition according to claim 1, wherein said composition is in the form of a tablet, a solution, a sachet or is contained within a gelatin capsule.

9. A method for treating hypoglycaemia in a patient suffering from non-insulin dependent diabetes comprising administering to said patient metformin, optionally in the form of one of its pharmaceutically acceptable salts, and a fibrate chosen from bezafibrate and fenofibrate.

10. A method according to claim 9, wherein said patient is non-dyslipidaemic.

11. A method according to claim 9, wherein metformin is in the form of a salt which is a hydrochloride, a fumarate, an embonate or a chlorophenoxyacetate.

12. A method according to claim 9, wherein metformin, or one of its pharmaceutically acceptable salts, and the fibrate are administered in a unit dose form.

13. A method according to claim 12, wherein said unit dose comprises from 100 to 1000 mg of metformin and from 50 to 300 mg of fenofibrate.

14. A method according to claim 12, wherein said unit dose comprises from 100 to 1000 mg of metformin and from 50 to 600 mg of bezafibrate.

15. A method according to claim 10, wherein metformin is in the form of a salt which is a hydrochloride, a fumarate, an embonate or a chlorophenoxyacetate.

16. A method according to claim 9, wherein metformin or one of its pharmaceutically acceptable salts and the fibrate are administered orally.

17. A method according to claim 9, wherein metformin or one of its pharmaceutically acceptable salts and the fibrate are administered parenterally.

18. A method according to claim 9, wherein metformin or one of its pharmaceutically acceptable salts is administered in a daily dosage of 100–2000 mg.

19. A method according to claim 18, wherein fenofibrate is administered in a daily dosage of 50–600 mg.

20. A method according to claim 18, wherein bezafibrate is administered in a daily dosage of 50–1200 mg.

21. A method according to claim 9, wherein metformin or one of its pharmaceutically acceptable salts is administered separately from the fibrate.

* * * * *